(12) United States Patent
Daga et al.

(10) Patent No.: US 9,188,574 B2
(45) Date of Patent: Nov. 17, 2015

(54) MOBILE GAS DETECTION CART WITH WIRELESS TRANSCEIVER

(75) Inventors: Dushyant R. Daga, Ridgefield, CT (US); Jennifer L. Gardner-Dimitri, Fishkill, NY (US); Michael A. Graziano, Washingtonville, NY (US); David M. Sweeney, II, New Fairfield, CT (US)

(73) Assignee: International Business Machines Corporation, Armonk, NY (US)

( * ) Notice: Subject to any disclaimer, the term of this patent is extended or adjusted under 35 U.S.C. 154(b) by 366 days.

(21) Appl. No.: 13/488,512

(22) Filed: Jun. 5, 2012

(65) Prior Publication Data

US 2013/0321148 A1   Dec. 5, 2013

(51) Int. Cl.
*G08B 1/08* (2006.01)
*G01N 33/00* (2006.01)

(52) U.S. Cl.
CPC ........ *G01N 33/0009* (2013.01); *G01N 33/0031* (2013.01)

(58) Field of Classification Search
CPC .............. G01N 33/0009; G01N 33/0031
USPC ................. 340/539.1, 539.11, 539.22
See application file for complete search history.

(56) References Cited

U.S. PATENT DOCUMENTS

| 5,959,529 A * | 9/1999 | Kail, IV .................... 340/539.12 |
| 6,026,667 A | 2/2000 | Takamoku |
| 6,228,657 B1 | 5/2001 | Genovese et al. |
| 6,532,801 B1 | 3/2003 | Shan et al. |
| 2004/0075566 A1 | 4/2004 | Stepanik et al. |
| 2006/0193262 A1 | 8/2006 | McSheffrey et al. |
| 2007/0100498 A1* | 5/2007 | Matsumoto et al. .......... 700/245 |
| 2012/0303160 A1* | 11/2012 | Ziegler et al. ................. 700/259 |
| 2013/0278753 A1* | 10/2013 | Guo et al. ..................... 348/114 |

FOREIGN PATENT DOCUMENTS

| CN | 1923456 | 3/2007 |
| CN | 201667109 | 12/2010 |
| CN | 201909771 | 7/2011 |
| CN | 201974402 | 9/2011 |
| DE | 4127543 | 2/1993 |
| EP | 2281668 | 9/2011 |
| WO | 2006071198 | 7/2006 |

OTHER PUBLICATIONS

Sadaki Nakano et al., "Hydrogen Gas Detection System Prototype with Wireless Sensor Networks", IEEE, pp. 159-162, 2005.
Office Action, Application No. 201310218351.5 Dated Jan. 4, 2015, pp. 1-13.

* cited by examiner

*Primary Examiner* — Daryl Pope
(74) *Attorney, Agent, or Firm* — Gibb & Riley, LLC (57) ABSTRACT

An apparatus comprises at least one frame, wheels operatively connected to the frame, at least one processor operatively connected to the frame, a plurality of gas detectors operatively connected to the processor, and at least one wireless transceiver operatively connected to the processor. Further, a rechargeable power storage unit is operatively connected to the processor, the gas detectors, and the wireless transceiver.

21 Claims, 6 Drawing Sheets

MOBILE GAS DETECTION CART WITH WIRELESS TRANSCEIVER

BACKGROUND

The present disclosure relates to gas detection equipment, and more specifically, to equipment for remote monitoring of gases.

Gas monitoring equipment is used to check for the presence of various chemicals within the gas environment of a specific space. For example, the air within a room is a gas/vapor environment within a specific space. Note that gas and vapors are referred to herein simply as gas, for convenience. If a room is to be used by humans without special breathing equipment, gas monitoring equipment can check the air within the room for gas phase chemicals and materials that may be harmful to humans, or that may harm the environment or other equipment.

However, such gas monitoring equipment is either limited to checking for a single gas, or is permanently installed in a single location, making its use limited. The embodiments described below address such situations.

SUMMARY

According to an embodiment herein, an exemplary apparatus comprises at least one frame, wheels operatively (directly or indirectly) connected to the frame, at least one processor operatively connected to the frame, a plurality of gas detectors operatively connected to the processor, and at least one wireless transceiver operatively connected to the processor. Further, a rechargeable power storage unit is operatively connected to the processor, the gas detectors, and the wireless transceiver.

According to a further embodiment herein, an exemplary apparatus comprises at least one frame, wheels operatively connected to the frame, at least one processor operatively connected to the frame, a plurality of gas detectors operatively connected to the processor, and at least one wireless transceiver operatively connected to the processor. The apparatus further comprises a graphic user interface operatively connected to the processor. Further, a rechargeable power storage unit is operatively connected to the processor, the gas detectors, the wireless transceiver, and the graphic user interface.

According to an additional embodiment herein, an exemplary apparatus comprises at least one frame, wheels operatively connected to the frame, at least one processor operatively connected to the frame, a plurality of gas detectors operatively connected to the processor, and at least one wireless transceiver operatively connected to the processor. The wireless transceiver connects to a wide area network. The apparatus further comprises a graphic user interface operatively connected to the processor. Further, a rechargeable power storage unit is operatively connected to the processor, the gas detectors, the wireless transceiver, and the graphic user interface.

According to another embodiment herein, an exemplary apparatus comprises at least one frame, wheels operatively connected to the frame, at least one processor operatively connected to the frame, a plurality of gas detectors operatively connected to the processor, and at least one wireless transceiver operatively connected to the processor. The wireless transceiver connects to the Internet. The apparatus further comprises a graphic user interface operatively connected to the processor and audible and visual warning elements operatively connected to the processor. Further, a rechargeable power storage unit is operatively connected to the processor, the gas detectors, the wireless transceiver, the graphic user interface, and the audible and visual warning elements.

BRIEF DESCRIPTION OF THE DRAWINGS

The embodiments herein will be better understood from the following detailed description with reference to the drawings, which are not necessarily drawing to scale and in which.

DETAILED DESCRIPTION

As mentioned above, gas monitoring equipment is either limited to checking for a single gas, or is permanently installed in a single location, making its use limited. The embodiments described below address such situations by providing a portable system for sensing potential hazardous gas concentrations in remote locations and, if needed, transmitting the concentration information to a communication device in a safe area. This unit/cart herein is typically used in emergency response, system start ups, trouble shooting equipment failure, investigation into odor complaint, checking gas cylinders at time of receipt, etc.

The cart comprises a mobile/portable hazardous gas detection system with wireless internet communication capabilities using a wireless router. Further, the cart includes various hazardous gas sensors (that are traditionally non-portable) mounted on a frame or brackets within the cart. The cart is powered by its own self-contained power supply, such as a battery or uninterrupted power supply (UPS). All the gas sensors can be programmed through a programmable logic controller (PLC) within the gas cart or programmed from the transmitter key pad of the sensor. A user interface, such as a flat screen panel, displays gas sensor levels, detector information, trending, warning and alarm set points, faults, and alarms. The cart is also equipped with a horn and light strobe to annunciate if alarm levels are found. The cart has the capability to sense gas levels at a remote location and transmit the gas concentration(s) to computers/laptops/communication devices (smart phones).

Figure 1:
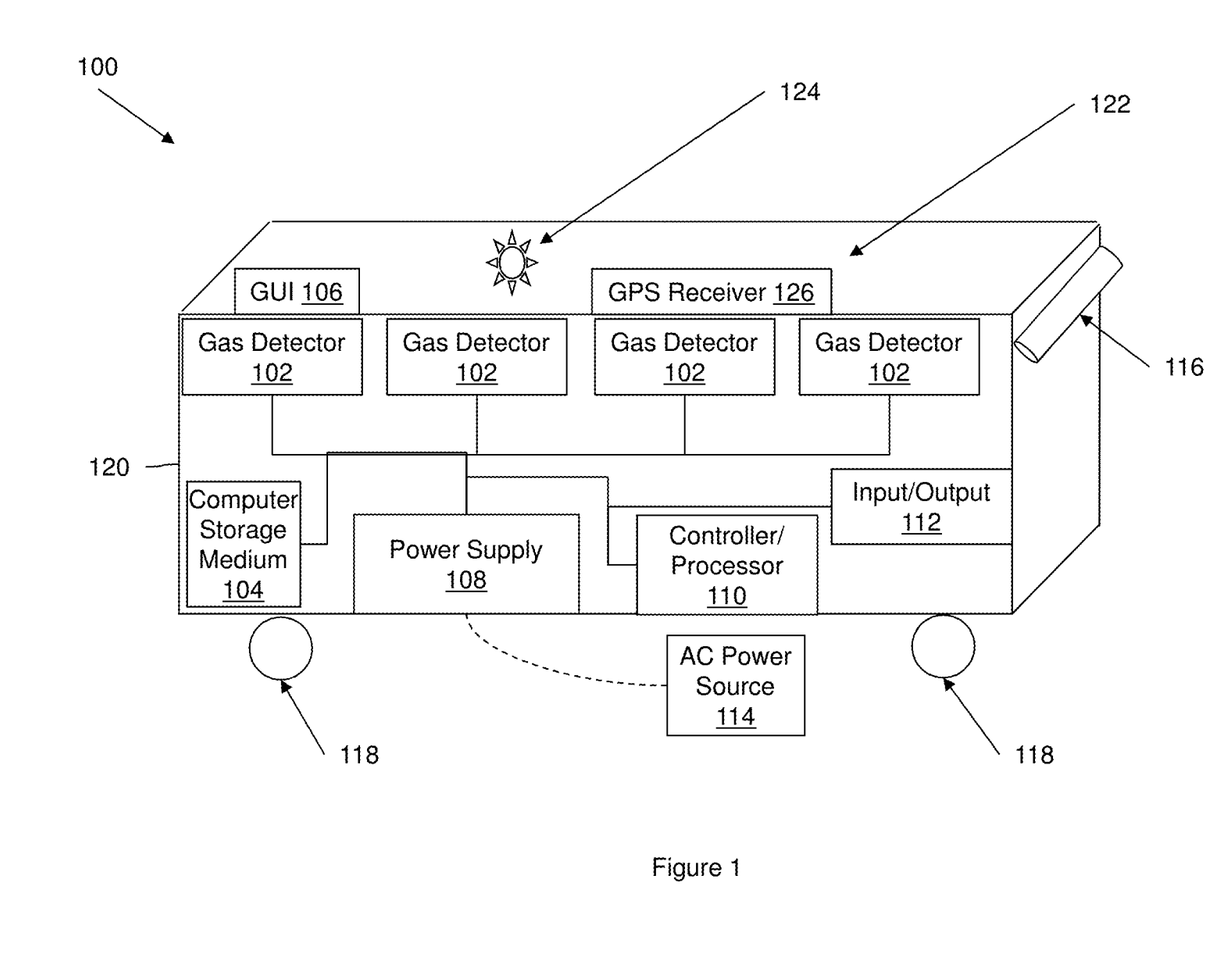
FIG. 1 is a schematic diagram illustrating a gas detection cart according to embodiments herein.

FIG. 1 illustrates one exemplary embodiment herein that comprises a gas cart 100 having at least one frame 120, wheels 118 operatively connected to the frame 120, at least one processor 110 operatively connected to the frame 120, a plurality of gas detectors 102 operatively connected to the processor 110, and at least one wireless transceiver 112 operatively connected to the processor 110. The gas cart 100 can also include a global positioning system (GPS) receiver or other position sensing/detecting device 126. The apparatus further comprises a graphic user interface 106 (such as a touch screen) operatively connected to the processor 110 and audible and visual warning elements 124 operatively connected to the processor 110. Further, a rechargeable power storage unit (or any other uninterruptible power supply) 108 is operatively connected to the processor 110, the gas detectors 102, the wireless transceiver 112, the graphic user interface 106, and the audible and visual warning elements.

The power storage unit 108 can be the only source of power supplied to the processor 110, the gas detectors 102, the wireless transceiver 112, the graphic user interface 106, and the audible and visual warning elements 124 (alternatively such elements can be connected to a constant power source). The power storage unit 108 can comprise, for example, a battery. The graphic user interface 106 displays gas sensor levels, detector information, trending, warning and alarm set points, faults, alarms, gas sensor cell life, battery level, and sensor(s) health.

In addition, the apparatus can include a cover 122 that is operatively connected to the frame 120. The cover encloses the processor 110, the gas detectors 102, the wireless transceiver 112, the graphic user interface 106, and the audible and visual warning elements. In some embodiments, the wheels 118 are driven and controlled by the processor 110. In addition, at least one handle 116 can be operatively connected to the frame 120.

Figure 2:
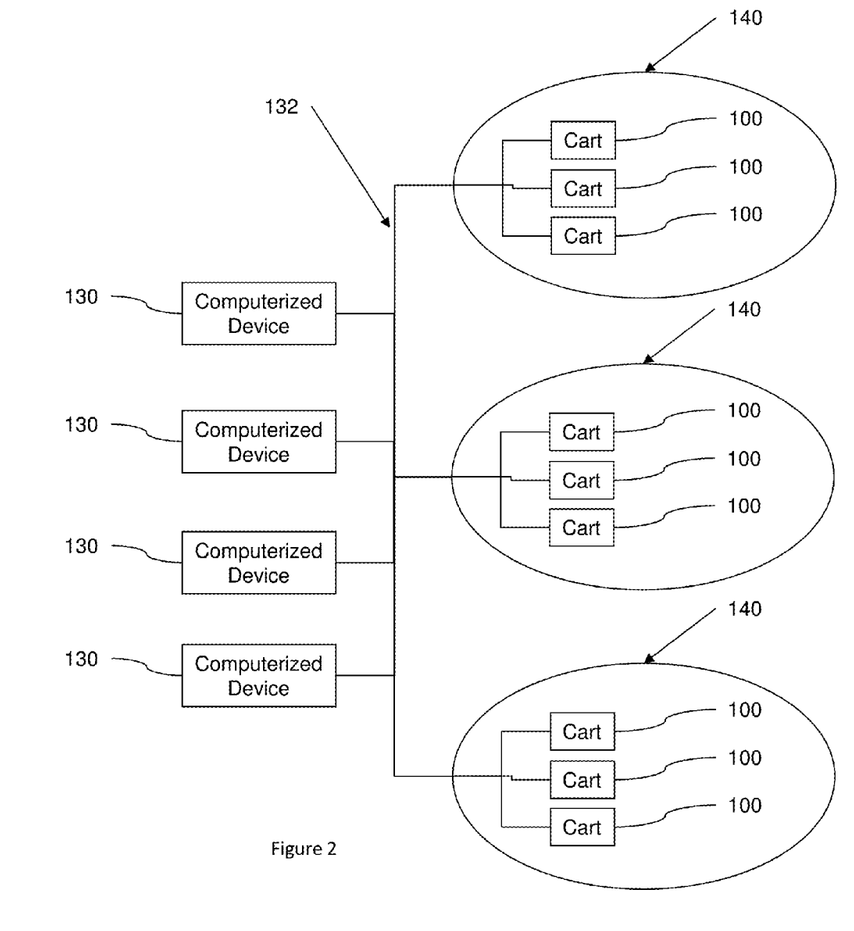
FIG. 2 is a schematic diagram illustrating a gas detection cart system according to embodiments herein.

The wireless transceiver 112 connects to a wide area network, such as the Internet. Therefore, as shown in FIG. 2, many gas carts 100 (physically located at different locations 140) can be connected to computerized devices 130 by way of a local or wide area network 132. Further, such a wireless connection 112 allows the gas detectors 102 to be remotely enabled and remotely monitored.

Therefore, the monitoring screens of graphic user interfaces discussed below could be on the gas cart 100 itself, or could be on computerized devices 130 located a safe distance from the location of the gas cart 100 or both. This allows the gas cart 100 to be moved from location 140 to location 140, while still being monitored from a central computer. Further, the GPS or other position sensor 126 allows the central computer to not only know where the gas cart is located, but also the atmospheric conditions at that location. Therefore, if many gas carts are monitored from a single central location, the position and gas readings from each can be easily understood. Additionally, the gas cart 100 can be remotely monitored by many different individuals who may be at many locations different than the gas cart 100.

Figure 3:
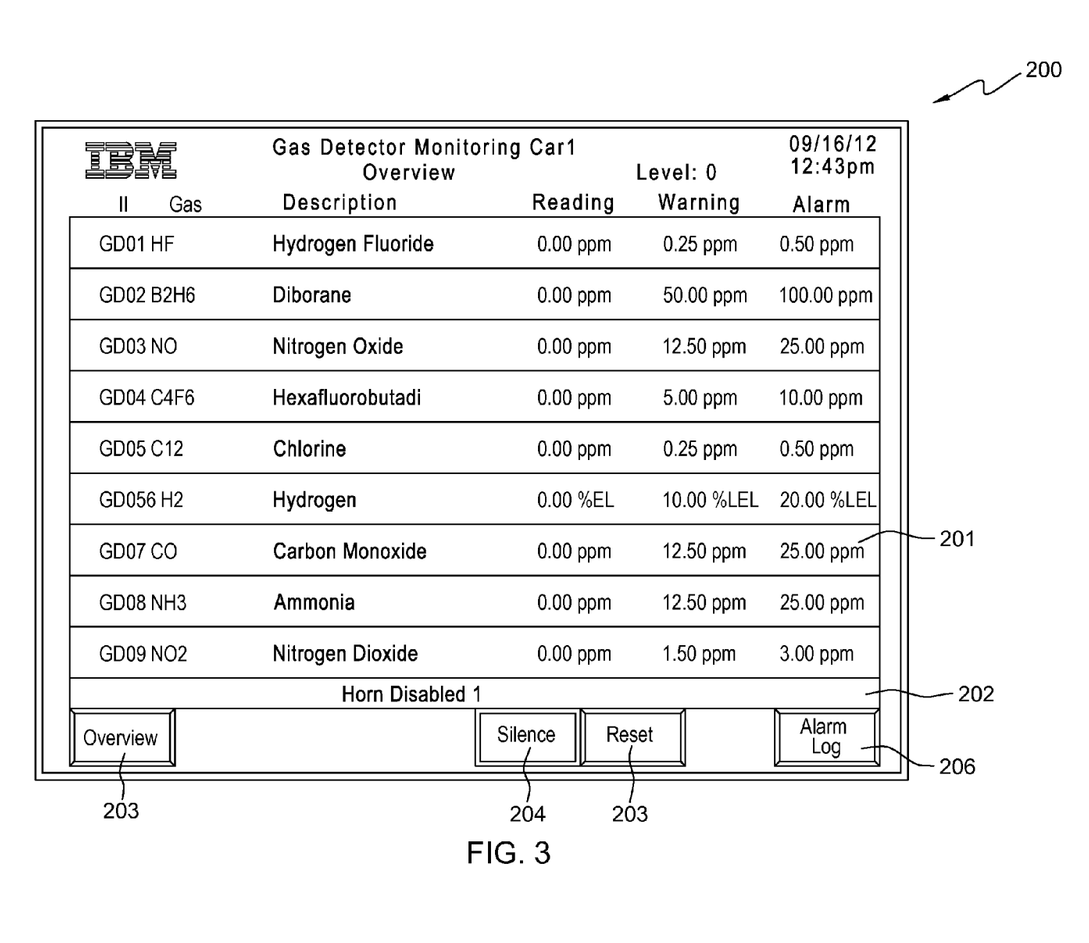
FIG. 3 is a schematic diagram illustrating a display produced by a gas detection cart according to embodiments herein.

FIG. 3 illustrates an exemplary screenshot 200 provided by the graphic user interface 106. As shown, this screenshot 200 displays readings of all gas Midas detectors on the cart 201 and warning & alarm set points 202. The alarm banner 202 will turn pink if in fault, blue if in trouble, yellow if gas detector reaches warning level and red if gas detector reaches alarm level. Further, the display 200 includes an overview button 203, a silence alarm button 204, a reset button 205, and an alarm log 206.

For example, the display can be set to provide a warning (banner 202 will turn yellow) when half of the occupational exposure limit is reached, and the full alarm (banner 202 will turn red) can be provided (including lights and sounds) at the occupational exposure limits for the gas.

Figure 4:
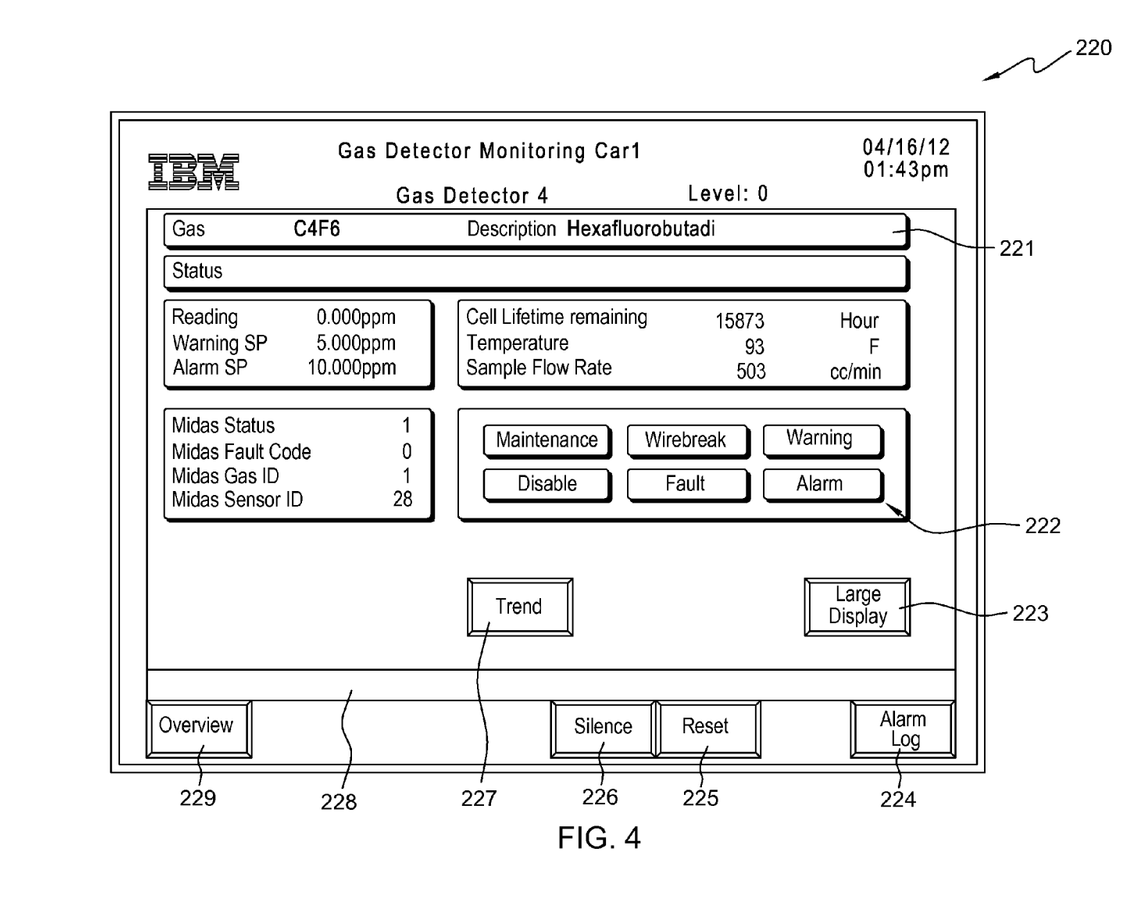
FIG. 4 is a schematic diagram illustrating a display produced by a gas detection cart according to embodiments herein.

FIG. 4 illustrates an exemplary screenshot 220 provided by the graphic user interface 106. As shown, this screenshot 220 displays the sensor readings 221, the status indicators 222, a "large display" button 223 (that is used for viewing the GUI from a distance), the alarm log 224, a reset button 225, a silence alarm button 226, a trend button 227, an alarm banner 228, and an overview display 229.

To view the gas real-time detection levels in large font, a user can touch the "large display" button 223 on the screen on lower right hand side. To view trending information a user can touch the trend button 227 on the screen (lower middle of screen). The default setting shows the trends for the last 9 minutes. The various trend indicators include a green line for the current reading, a yellow line for the warning set point, and a red line for the alarm set point. The calendar in the upper left hand corner of display can be used to view previous dates and times.

The audible alarm and strobe only activates if concentration is detected at or above the alarm set point levels. The alarms (audible & strobe) can be optionally disabled only with the use a password.

Figure 5:
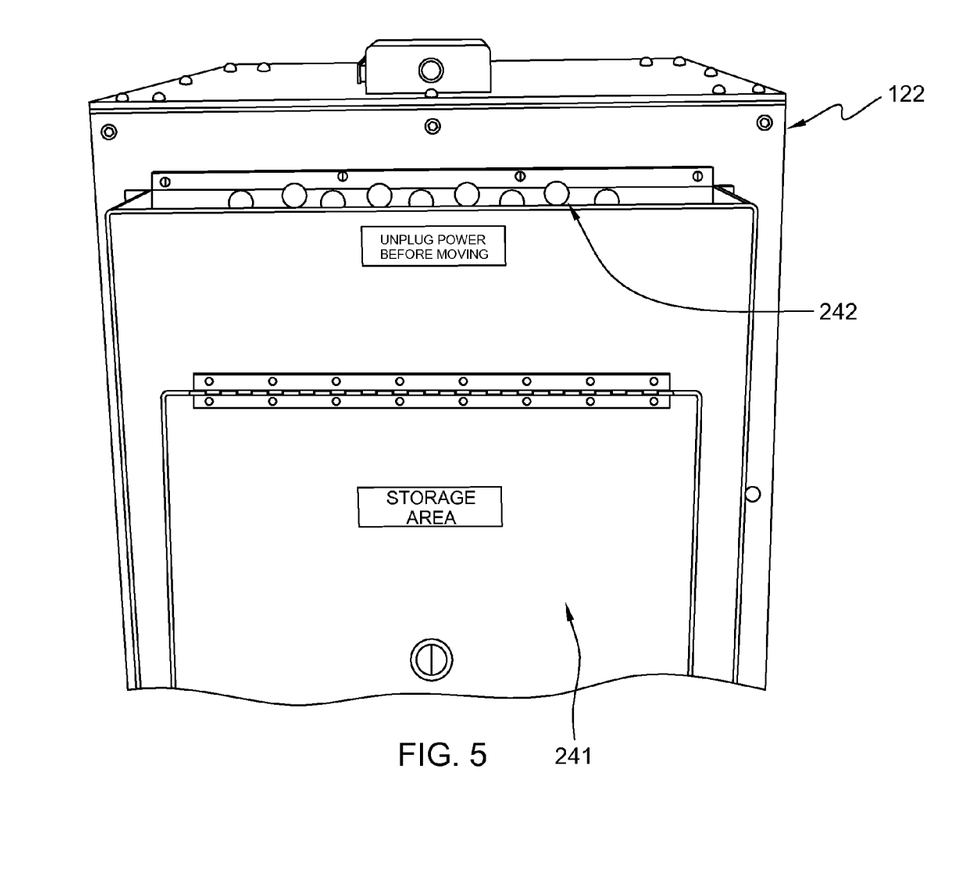
FIG. 5 is a schematic diagram illustrating a display produced by a gas detection cart according to embodiments herein.

FIG. 5 illustrates the outer cover 122 in greater detail. The outer cover 122 can include openings for sample tube ports that allow gases to be drawn into the gas detectors and can also include a storage area 241 for storing sample tubes 242.

The sensors that are within the gas cart 100 include a sensor for sensing Hydrogen Fluoride, Hydrogen Chloride, Hydrogen Bromide, Boron Trichloride, Germanium Tetrafluoride, Tungsten Hexafluoride, Dichlorosilane, Silicon Tetrafluoride, Boron Trifluoride, halogen groups, etc. Further, another sensor is included to sense Diborane, Germane, Phosphine, Arsine, Digermane, Silane, Disilane, Trimethylsilane, etc. An additional sensor is used to sense Nitric Oxide. Also, another sensor is used to sense 1,3-Hexafluorobutadiene, Nitrogen Trifluoride, Difluoromethane, Methyl Fluoride, perfluoro compounds, etc. Another sensor is used to sense Chlorine, Fluorine, etc. A sensor is used to sense Hydrogen, Propene, Propane, Acetylene, Ethylene, Methyl Fluoride, Methane, Difluromethane, Ethane, flammable items, etc. Also, an additional sensor is used to sense Carbon Monoxide, etc. A NH3 (ammonia) sensor is used to sense ammonia, etc. Also, a NO2 (Nitrogen Dioxide) sensor is used to sense Nitrogen Dioxide, etc. While a limited number of sensors have been mentioned above, those ordinarily skilled in the art would understand that these sensors are merely exemplary and that the gas carts herein could include many more gas sensors, whether now known or developed in the future.

As will be appreciated by one skilled in the art, aspects of the systems and methods herein may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium (s) having computer readable program code embodied thereon.

Any combination of one or more computer readable non-transitory medium(s) may be utilized. The computer readable medium may be a computer readable signal medium or a computer readable storage medium. The non-transitory computer storage medium stores instructions, and a processor executes the instructions to perform the methods described herein. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments herein. It will be understood that each block of the flowchart illustrations and/or two-dimensional block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 6:
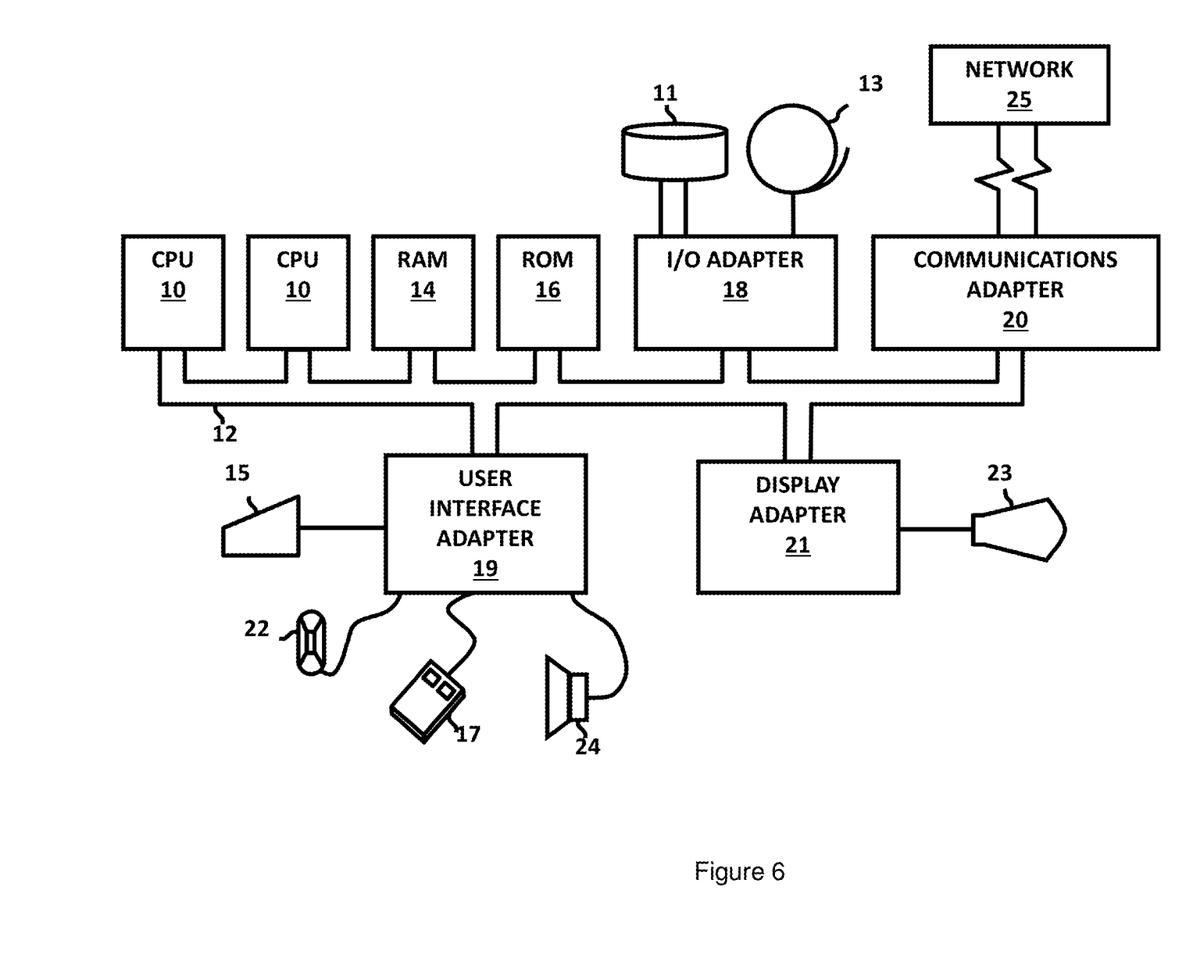
FIG. 6 is a schematic diagram of a hardware system according to embodiments herein.

A representative hardware environment for practicing the embodiments herein is depicted in FIG. 6. This schematic drawing illustrates a hardware configuration of an information handling/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The flowchart and block diagrams in the Figures illustrate the architecture, functionality, and operation of possible implementations of systems, methods and computer program products according to various embodiments herein. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus comprising:
at least one frame;
wheels operatively connected to said frame;
at least one processor operatively connected to said frame;
a plurality of gas detectors operatively connected to said processor, said gas detectors evaluating atmospheric conditions where said apparatus is located, and different ones of said gas detectors detecting different hazardous gasses;
at least one wireless transceiver operatively connected to said processor;
a position sensing device operatively connected to said processor, said position sensing device determining a location of said apparatus; and a rechargeable power storage unit operatively connected to said processor, said gas detectors, and said wireless transceiver,
said wheels being driven,
said wheels being controlled by said processor,
said processor maintaining warning and alarm set points,
said processor determining gas sensor levels, detector information, trending of gas levels over time, faults, and alarms based on output from said gas detectors, and
said processor communicating with a second computerized device that is at a different location than said apparatus using said wireless transceiver to provide said second computerized device with said gas sensor levels, said detector information, said trending of gas levels over time, said warning and alarm set points, said faults, said alarms, and said location of said apparatus.

2. The apparatus according to claim 1, said power storage unit comprising the only source of power supplied to said processor, said gas detectors, and said wireless transceiver.

3. The apparatus according to claim 1, said power storage unit comprising a battery.

4. The apparatus according to claim 1, further comprising a cover operatively connected to said frame,
said cover enclosing said processor, said gas detectors, and said wireless transceiver.

5. The apparatus according to claim 1, further comprising a graphic user interface operatively connected to said processor, said graphic user interface displaying said gas sensor levels, said detector information, said trending of gas levels over time, said warning and alarm set points, said faults, and said alarms.

6. An apparatus comprising:
at least one frame;
wheels operatively connected to said frame;
at least one processor operatively connected to said frame;
a plurality of gas detectors operatively connected to said processor, said gas detectors evaluating atmospheric conditions where said apparatus is located, and different ones of said gas detectors detecting different hazardous gasses;
at least one wireless transceiver operatively connected to said processor;
a position sensing device operatively connected to said processor, said position sensing device determining a location of said apparatus; and
a graphic user interface operatively connected to said processor; and
a rechargeable power storage unit operatively connected to said processor, said gas detectors, said wireless transceiver, and said graphic user interface,
said wheels being driven,
said wheels being controlled by said processor,
said processor maintaining warning and alarm set points,
said processor determining gas sensor levels, detector information, trending of gas levels over time, faults, and alarms based on output from said gas detectors, and
said processor communicating with a second computerized device that is at a different location than said apparatus using said wireless transceiver to provide said second computerized device with said gas sensor levels, said detector information, said trending of gas levels over time, said warning and alarm set points, said faults, said alarms, and said location of said apparatus.

7. The apparatus according to claim 6, said power storage unit comprising the only source of power supplied to said processor, said gas detectors, said wireless transceiver, and said graphic user interface.

8. The apparatus according to claim 6, said power storage unit comprising a battery.

9. The apparatus according to claim 6, further comprising a cover operatively connected to said frame,
said cover enclosing said processor, said gas detectors, said wireless transceiver, and said graphic user interface.

10. The apparatus according to claim 6, said graphic user interface displaying said gas sensor levels, said detector information, said trending of gas levels over time, said warning and alarm set points, said faults, and said alarms.

11. An apparatus comprising:
at least one frame;
wheels operatively connected to said frame;
at least one processor operatively connected to said frame;
a plurality of gas detectors operatively connected to said processor, said gas detectors evaluating atmospheric conditions where said apparatus is located, and different ones of said gas detectors detecting different hazardous gasses;
at least one wireless transceiver operatively connected to said processor, said wireless transceiver connecting to a wide area network;
a position sensing device operatively connected to said processor, said position sensing device determining a location of said apparatus; and
a graphic user interface operatively connected to said processor; and
a rechargeable power storage unit operatively connected to said processor, said gas detectors, said wireless transceiver, and said graphic user interface,
said wheels being driven,
said wheels being controlled by said processor,
said processor maintaining warning and alarm set points,
said processor determining gas sensor levels, detector information, trending of gas levels over time, faults, and alarms based on output from said gas detectors, and
said processor communicating with a second computerized device that is at a different location than said apparatus using said wireless transceiver to provide said second computerized device with said gas sensor levels, said detector information, said trending of gas levels over time, said warning and alarm set points, said faults, said alarms, and said location of said apparatus.

12. The apparatus according to claim 11, said power storage unit comprising the only source of power supplied to said processor, said gas detectors, said wireless transceiver, and said graphic user interface.

13. The apparatus according to claim 11, said power storage unit comprising a battery.

14. The apparatus according to claim 11, further comprising a cover operatively connected to said frame,
said cover enclosing said processor, said gas detectors, said wireless transceiver, and said graphic user interface.

15. The apparatus according to claim 11, said graphic user interface displaying gas sensor levels, detector information, trending, warning and alarm set points, faults, and alarms.

16. An apparatus comprising:
at least one frame;
wheels operatively connected to said frame;
at least one processor operatively connected to said frame;
a plurality of gas detectors operatively connected to said processor, said gas detectors evaluating atmospheric conditions where said apparatus is located, and different ones of said gas detectors detecting different hazardous gasses;
at least one wireless transceiver operatively connected to said processor;

a position sensing device operatively connected to said processor, said position sensing device determining a location of said apparatus;

said wireless transceiver connecting to the Internet;

a graphic user interface operatively connected to said processor;

audible and visual warning elements operatively connected to said processor; and a rechargeable power storage unit operatively connected to said processor, said gas detectors, said wireless transceiver, said graphic user interface, and said audible and visual warning elements, said wheels being driven, said wheels being controlled by said processor, said processor maintaining warning and alarm set points, said processor determining gas sensor levels, detector information, trending of gas levels over time, faults, and alarms based on output from said gas detectors, and said processor communicating with a second computerized device that is at a different location than said apparatus using said wireless transceiver to provide said second computerized device with said gas sensor levels, said detector information, said trending of gas levels over time, said warning and alarm set points, said faults, said alarms, and said location of said apparatus.

17. The apparatus according to claim 16, said power storage unit comprising the only source of power supplied to said processor, said gas detectors, said wireless transceiver, said graphic user interface, and said audible and visual warning elements.

18. The apparatus according to claim 16, said power storage unit comprising a battery.

19. The apparatus according to claim 16, further comprising a cover operatively connected to said frame, said cover enclosing said processor, said gas detectors, said wireless transceiver, said graphic user interface, and said audible and visual warning elements.

20. The apparatus according to claim 16, said graphic user interface displaying said gas sensor levels, said detector information, said trending, said warning and said alarm set points, said faults, and said alarms.

21. The apparatus according to claim 16, further comprising at least one handle operatively connected to said frame.

\* \* \* \* \*